United States Patent [19]

Christiansen

[11] 4,160,027
[45] Jul. 3, 1979

[54] STEROID CYANOKETONES AND INTERMEDIATES

[75] Inventor: Robert G. Christiansen, Schodack, N.Y.

[73] Assignee: Sterling Drug Inc., New York, N.Y.

[21] Appl. No.: 862,417

[22] Filed: Dec. 20, 1977

[51] Int. Cl.² ............... A61K 31/58; C07J 43/00
[52] U.S. Cl. ....................... 424/241; 260/239.55 R; 260/239.55 C; 260/239.5; 260/397.3
[58] Field of Search ............ 424/241; 260/239.55, 260/239.55 R, 239.55 C

[56] References Cited

U.S. PATENT DOCUMENTS 3,980,638   9/1976   Babcock et al. ............ 424/241
4,062,954   12/1977   Potts ......................... 424/241

*Primary Examiner*—Elbert L. Roberts
*Attorney, Agent, or Firm*—Thomas L. Johnson; B. Woodrow Wyatt

[57] ABSTRACT

2α-Cyano-3-oxosteroids having a 4α,5α-epoxy group and alkylated in the 4- and/or 6-position, useful as interceptive agents, are prepared by alkaline cleavage of the corresponding steroido[2,3-d]isoxazoles.

22 Claims, No Drawings

STEROID CYANOKETONES AND INTERMEDIATES

BACKGROUND OF THE INVENTION (a) Field of the Invention

This invention relates to novel 2α-cyano-3-oxosteroids having a 4α,5α-epoxy group and alkylated in the 4- and/or 6-position, to intermediates therefor, to methods for the preparation thereof, and to compositions and methods for the use thereof as interceptive agents.

(b) Description of the Prior Art

Clinton and Manson U.S. Pat. No. 3,296,255, issued Jan. 3, 1967 discloses certain 2α-cyano-3-oxosteroids and intermediates therefor as follows:

(1) 2α-Cyano-3-oxosteroids:

Example 16(b) 2α-cyano-4α,5α-epoxyandrostan-17β-ol-3-one

Example 17(b) 2α-cyano-4α,5α-epoxy-17α-ethynylandrostan-17β-ol-3-one

EXAMPLE 18(b) 2α-cyano-4α,5α-epoxy-17α-methylandrostan-17β-ol-3-one

Example 34 2α-cyano-6α,17α-dimethyl-4-androsten-17β-ol-3-one

Example 55 2α-cyano-4-methyl-4-androsten-17β-ol-3-one

Example 56 2α-cyano-4,17α-dimethyl-4-androsten-17β-ol-3-one (2) Intermediate isoxazoles:

Example 16(a) 17β-acetoxy-4α,5α-epoxyandrostano[2,3-d]isoxazole

Example 17(a) 4α,5α-epoxy-17β-hydroxy-17α-ethynylandrostano[2,3-d]isoxazole

Example 18(a) 4α,5α-epoxy-17β-hydroxy-17α-methylandrostano[2,3-d]isoxazole

Example 34 6α,17α-dimethyl-17β-hydroxy-4-androsteno[2,3-d]isoxazole

Example 55 4-methyl-17β-hydroxy-4-androsteno[2,3-d]isoxazole

Example 56 4,17α-dimethyl-17β-hydroxy-4-androsteno[2,3-d]isoxazole

The 2α-cyano-3-oxosteroids of U.S. Pat. No. 3,296,255 are stated to possess endocrinological and pharmacological activity, for example, adrenal inhibiting, pituitary inhibiting, electrolyte modifying, hypotensive and coronary dilator properties.

At the Conference on Medicinal Chemistry of the Gordon Research Conference, August 1976, it was disclosed by Gordon O. Potts, H. Philip Schane, Jr. and Robert G. Christiansen that 2α-cyano-4α,5α-epoxyandrostan-17β-ol-3-one was effective in disrupting pregnancy in rats at an oral dose of 500 mg/kg when administered ten days after insemination, and in monkeys at a dose of 500 mg/monkey for five days; and that 2α-cyano-4α,5α-epoxy-17α-methylandrostan-17β-ol-3-one was similarly effective in rats at an oral dose of 500 mg/kg.

SUMMARY OF THE INVENTION

In a composition of matter aspect, the invention relates to compounds of the formula

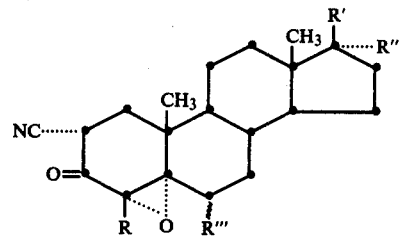

wherein:

R is hydrogen or methyl;

R' is hydroxy or lower-alkanoyloxy;

R" is hydrogen, lower-alkyl, lower-alkenyl or lower-alkynyl; or R' and R" together represent oxo or ethylenedioxy;

R''' is hydrogen or methyl; or 3-enol lower-alkanoate esters thereof; with the proviso that when R is hydrogen, R''' is α-methyl; and when R is methyl, R''' is hydrogen or β-methyl.

The compounds of the invention are useful as interceptive agents; that is, they disrupt pregnancy when administered to pregnant female mammals, causing elimination of the fetus or fetuses.

In a process aspect, the invention relates to a process for preparing a compound of formula I from a compound of the formula

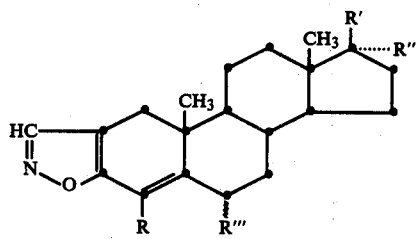

wherein R, R', R" and R''' have the meanings given above by epoxidizing the 4,5-double bond with hydrogen peroxide or a peracid, and cleaving the isoxazole ring with a base to produce the cyanoketone, the reactions being carried out in either order.

In a further composition of matter aspect, the invention relates to a composition for disrupting pregnancy which comprises an interceptively effective amount of a compound of formula I incorporated in a pharmaceutical carrier suitable for oral administration.

In a further process aspect, the invention relates to a method for disrupting pregnancy in a female mammal which comprises administering orally to said mammal, subsequent to implantation of a fertilized ovum in said mammal, an interceptively effective amount of a compound of formula I.

In a further composition of matter aspect, the invention relates to compounds of the formula

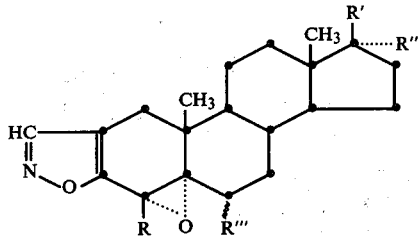

wherein:
R is hydrogen or methyl;
R' is hydroxy;
R" is hydrogen, lower-alkyl, lower-alkenyl or lower-alkynyl; or R' and R" together represent oxo or ethylenedioxy; and
R'" is hydrogen or methyl; with the proviso that when R is hydrogen, R'" is α-methyl; and when R is methyl, R'" is hydrogen or β-methyl; and also to certain additional novel intermediates.

DETAILED DESCRIPTION INCLUSIVE OF PREFERRED EMBODIMENTS

The compounds of the invention are prepared from a known class of steroid compounds having the formula

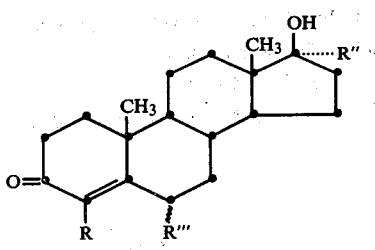

A compound of formula IV is caused to react with a lower-alkyl formate in the presence of a base whereby a hydroxymethylene group (OCHC=) is introduced at the 2-position of the steroid nucleus. The resulting hydroxymethylene derivative is then interacted with hydroxylamine, preferably in acidic aqueous medium, to give a compound of formula II.

The conversion of a compound of formula II to a compound of formula I requires the introduction of an epoxide at the 4,5-position and the cleavage of the isoxazole ring. The two reactions can be carried out in either sequence although it is preferred that the ring cleavage occur as the last step. The cleavage of the isoxazole ring to a cyanoketone is effected in basic medium at ambient temperature, preferably in an inert solvent with a strong base such as sodium methoxide or other alkali metal alkoxide, or an alkali metal hydroxide such as potassium hydroxide. The introduction of the epoxide is effected by treating the 4,5-unsaturated compound with a peroxide compound, for example, hydrogen peroxide; alkylhydroperoxides such as t-butylhydroperoxide; and peracids such as m-chloroperbenzoic acid, p-nitroperbenzoic acid, peracetic acid, perbenzoic acid, permaleic acid, perphthalic acid, and the like.

The compounds of formula I where R' is lower-alkanoyloxy and the 3-enol lower-alkanoate esters are prepared by conventional esterification reactions as by treatment with the appropriate acid halide or acid anhydride. The enol esters are generally formed more readily and cleaved more readily than the 17-esters, especially when R" is other than hydrogen. Therefore, the ester groups can be introduced and removed selectively. The lower-alkanoyloxy groups preferably have from one to six carbon atoms, thus including such groups as formyloxy, acetoxy, propionyloxy, butyryloxy, isobutyryloxy, hexanoyloxy, and the like.

When R" in the compounds of formulas I, II or III is lower-alkyl, lower-alkynyl or lower-alkenyl, the groups can possess from one to three carbon atoms, thus including such groups as methyl, ethyl, propyl, isopropyl, ethynyl, 1-propynyl, 2-propynyl, vinyl, allyl and 1-propenyl.

Endocrinological evaluation of the compounds of formula I and certain species of the intermediates of formulas II and III has shown that they are useful in disrupting pregnancy in female mammals upon oral administration subsequent to conception. Interceptive activity was evaluated in Sprague-Dawley female rats as follows: vaginal smears were taken and read for the presence of spermatozoa following overnight mating. The day spermatozoa were found was designated as day one of pregnancy. The test compound was administered orally in a single dose on day ten of pregnancy at varying dose levels in different groups of rats. On the fifteenth day after insemination, the rats were killed with an overdose of sodium pentobarbital and the uterine implantation sites were counted. Each implantation site was assessed as being a developing fetus, a dead fetus or a resorption site. The minimum effective dose in 100% of the animals (MED$_{100}$) was then determined.

A composition aspect of the invention comprises an interceptively effective amount of a compound of formula I incorporated in an inert pharmaceutical carrier. Said composition is prepared by dissolving or suspending it in a pharmaceutically acceptable liquid vehicle, e.g. aqueous alcohol, glycol, cottonseed oil solution or oil-water emulsion, gum tragacanth suspension, or the like; or by incorporating it in unit dosage form as tablets or capsules either alone or in combination with conventional adjuvants, e.g. calcium carbonate, starch, lactose, talc, magnesium stearate, gum acacia, and the like. Illustrative capsule mix formulations are as follows:

|  | mg/capsule | mg/capsule |
| --- | --- | --- |
| Compound I (micronized) | 100 | 200 |
| Starch | 62 | 76.6 |
| Lactose | 62 | 76.6 |
| Talc | 5 | 5 |
| Magnesium stearate | 1 | 1.8 |
| Net Weight | 230 | 360 |

In the method aspect of the invention, a compound of formula I is preferably administered in a daily dose of between 25 and 500 mg/kg of body weight for a period of between one and five days; and preferably at a time at least about 8 days after exposure to insemination.

The following examples will further illustrate the invention without the latter being limited thereby.

EXAMPLE 1

(a) 17β-Hydroxy-17-methyl-4-(phenylthiomethyl)androst-4-en-3-one

A mixture of 904 g. (3 m.) of 17α-hydroxy-17-methyl-androst-4-en-3-one, 650 ml. (6.3 m.) of thiophenol, 560 ml. of 38% formaldehyde, 680 ml. of triethylamine and 1.7 l. of absolute alcohol was heated at reflux for 55 hours and then cooled to room temperature. The light brown solution was quenched in 16 l. of 0.5N aqueous potassium hydroxide and stirred for 20 minutes until a uniformly dispersed suspension had been formed. The product was collected by filtration using coarse filter paper and the filter cake was washed with 5 × 1.5 l. of water. The solid was slurried in 4 l. of water, separated on a funnel and washed again thoroughly with water until the filtrate was neutral. In order to reduce the odor of thiophenol the filter cake was washed 5 times with 100 ml. of n-hexane and then it was dried at 40° C. in vacuo. Recrystallization of the crude material from 6.5 l. of absolute alcohol, washing with alcohol and drying at 30°–50° C. in vacuo yielded three crops of product, 762 g. (m.p. 133°–138° C.), 141 g. (m.p. 121°–128° C.) and 41 g. (m.p. 123°–130° C.). The purity of the second and third crops was identical with that of the first crop by TLC analysis. Therefore, all crops were combined for a total yield of 979 g. (75%) of 17β-hydroxy-17-methyl-4-(phenylthiomethyl)androst-4-en-3-one.

(b) 17β-Hydroxy-4,17-dimethylandrost-4-en-3-one

Into a 22 l. 3-necked flask equipped with an efficient stirrer, nitrogen inlet tube, dropping funnel and a condenser was placed 1.8 l. of Raney nickel-water sludge (W. Grace Co., No. 42000). A slow stream of nitrogen was applied and the catalysts was washed thoroughly with 3 × 4 l. of water followed by 4 × 4 l. of acetone. After the last acetone wash, the catalyst was suspended in 9 l. of fresh acetone and a warm solution (about 40° C.) of 520 g. of 17β-hydroxy-17-methyl-4-(phenylthiomethyl)androst-4-en-3-one in 3 l. of acetone was added from a dropping funnel with good stirring over a 10 minute period. The temperature was brought to reflux cautiously and gentle refluxing was continued for 5 hours. Stirring with no heat was maintained overnight and then the Raney nickel was allowed to settle for about 2 hours. The supernatant liquid was removed by suction and the catalyst was washed 4 times with 4 l. of acetone. The combined main portion and the washes were filtered through a filter aid and concentrated to a total volume of about 1 liter. The resulting thick slurry was cooled, filtered and the filter cake was washed with 2 × 50 ml. of cold acetone and then with 3 × 200 ml. of n-hexane. After drying the product at 60° C. in vacuo it weighed 316 g. and melted at 141°–144° C., an 82% yield of 17β-hydroxy-4,17-dimethylandrost-4-en-3-one.

(c) 17β-Hydroxy-2-hydroxymethylene-4,17-dimethylandrost-4-en-3-one

A clear solution of 620 g. (1.95 m.) of 17β-hydroxy-4,17-dimethylandrost-4-en-3-one in 5.5 l. of dry tetrahydrofuran and 12 ml. of methanol was stirred at room temperature under nitrogen and 280 g. (5 m.) of sodium methoxide was added all at once. As soon as a uniform suspension had been formed, 610 ml. (10 m.) of methyl formate was introduced from a dropping funnel over a period of 1.5 hours. The temperature was maintained at 20°–50° C. by intermittent cooling. Stirring was then continued for an additional 20 hours. The reddish brown mixture was diluted with 720 ml. of distilled water and concentrated in vacuo to about 2.5 l. volume. The residue was dissolved in 4.5 l. of water, charcoaled, filtered through a layer of filter aid and placed in a 12 l. battery jar surrounded by an ice bath. The mixture was cooled to 8° C. and 800 ml. of 6N HCl was added dropwise with efficient stirring until the pH was lowered to about 3. The acidification was completed in 2.5 hours, the resulting thick suspension was stirred at 5° C. for an additional 1.5 hours and then it was filtered. Thorough washing with water (4 × 100 ml.) and drying at 60° C. in vacuo yielded 641 g. (98%) of 17β-hydroxy-2-hydroxymethylene-4,17-dimethylandrost-4-en-3-one as a light yellow product, m.p. 182°–188° C.

(d) 4,17-Dimethylandrosta-2,4-dieno[2,3-d]isoxazol-17β-ol [II; R and R'' are CH$_3$, R' is OH, R''' is H]

A mixture of 746 g. (2.17 m.) of 17β-hydroxy-2-hydroxymethylene-4,17-dimethylandrost-4-en-3-one and 6.5 l. of glacial acetic acid was stirred vigorously and a solution containing 165 g. (2.4 m.) of hydroxylamine hydrochloride and 335 g. (2.46 m.) of sodium acetate trihydrate in 1 l. of water was added all at once. Stirring at room temperature was continued for a period of 6 hours. A total of 4.5 l. of water was added over a period of about 15 minutes to the resulting suspension, the mixture was stirred for an additional 15 minutes and the solid material was filtered off. The solid was washed with water (4 × 250 ml.) and n-hexane (1 × 250 ml.) and dried at 50° C. in vacuo overnight to yield 695 g. of crude product melting at 170°–178° C. The entire batch was recrystallized by dissolving it in 7 l. of absolute alcohol and 250 ml. of methanol and then by chilling to 5° C. A second crop was obtained from approximately 3.5 l. of volume. The filter cakes were washed with cold alcohol followed by n-hexane and dried at 50° C. in vacuo to give 430 g. of first crop material, m.p. 189°–192° C. and 107 g. of second crop material, m.p. 189°–192° C. The mother liquor was concentrated in vacuo and two more crops were isolated: 66 g., m.p. 183°–185° C. and 41 g., m.p. 167°–177° C. They were recrystallized from 700 ml. of alcohol, and the white product was slurried in 150 ml. of isopropyl acetate, filtered and dried at 50° C. in vacuo to give an additional 64 g. of good material, m.p. 190°–194° C. which was combined with the first two crops for a total of 607 g. (82%) of 4,17-dimethylandrosta-2,4-dieno[2,3-d]isoxazol-17β-ol.

(e) 4α,5α-Epoxy-4,17-dimethylandrost-2-eno[2,3-d]isoxazol-17β-ol [III; R and R'' are CH$_3$, R' is OH, R''' is H]

537 g. (1.57 m.) of 4,17-dimethylandrosta-2,4-dieno[2,3-d]isoxazol-17β-ol was dissolved in 4 l. of methylene dichloride and the solution was decolorized with charcoal. The filtrate was placed in a 22 l. 3-necked flask, diluted with an additional 3 l. of methylene dichloride and cooled to 3° C. Over a period of 40 minutes 375 g. (1.75 m.) of 80% m-chloroperbenzoic acid was added portionwise with efficient stirring while the temperature was maintained below 5° C. The mixture was stirred in an ice bath for 6 hours and then overnight at room temperature. The mixture was cooled to 5° C. and the excess m-chloroperbenzoic acid was decomposed by adding aqueous sodium sulfite solution (50 g. of Na$_2$SO$_3$ in 2 l. of water). The two phase mixture was stirred for five minutes, filtered in order to remove the solid m-chlorobenzoic acid, and the filter cake was washed with 500 ml. of methylene dichloride. The combined filtrates were treated with sodium bicarbonate solution until neutral. The organic layer was washed with 2 l. of water followed by 2 l. of brine. The combined aqueous layers were reextracted once with 1 l. of methylene dichloride and the extract was combined with the main organic portion. The solution was dried over anhydrous sodium sulfate, decolorized with charcoal, concentrated to a total volume of 3 l. and cooled to 10° C. The product was filtered, washed with cold isopropyl alcohol (2 × 50 ml.) and n-hexane (3 × 100 ml.), and then it was dried at 60° C. in vacuo to give 331 g. (crop A), m.p. 221°–224° C.

From the filtrate three additional crops were isolated by concentration and cooling:

B. 98 g., m.p. 215°–217° C.
C. 16 g., m.p. 187°–192° C.
D. 15 g., m.p. 185°–192° C.

Crop B was crystallized from 330 ml. of dimethylformamide to yield 94 g. of good material, m.p. 235°–239° C. (crop E). Crops C and D were added to the filtrate and the mixture was heated until a clear solution resulted. By cooling the solution an additional 23 g. of the product (m.p. 225°–233° C.) was recovered and combined with crops A and E for a total yield of 448 g. (80%) of 4α,5α-epoxy-4,17-dimethylandrost-2-eno[2,3-d]isoxazol-17β-ol. A sample of the compound when recrystallized from a tetrahydrofuran—ethanol mixture was obtained in the form of colorless matted needles, m.p. 244°–252° C.; $[\alpha]_D^{25} = +67.7°$ (1% in chloroform).

(f) 4α,5α-Epoxy-17β-hydroxy-4,17-dimethyl-3-oxoandrostane-2α-carbonitrile [I; R and R″ are CH$_3$, R′ is OH, R‴ is H]

In a 12 l., 3-necked flask were placed 7 l. of dry tetrahydrofuran and 425 g. (1.2 m.) of 4α,5α-epoxy-4,17-dimethylandrost-2-eno[2,3-d]isoxazol-17β-ol. The mixture was stirred vigorously and 128 g. (2.4 m.) of sodium methoxide was added portionwise under a continuous stream of nitrogen. Stirring of the mixture at room temperature was continued for an additional 2 hours, and the suspension was then quenched in 26 l. of cold water to which had been added 210 ml. of concentrated hydrochloric acid. The solid was filtered, washed with 3 × 200 ml. of water, slurried in 6 l. of water, filtered, washed with 3 × 100 ml. of water and dried at 35° C. in vacuo for three days. The resulting product which still contained some water and melted at 166°–167° C. was powdered and redried at 55° C. for 24 hours. A total of 409 g. (96%) of 4α,5α-epoxy-17β-hydroxy-4,17-dimethyl-3-oxoandrostane-2α-carbonitrile was obtained; m.p. 172°–174° C. A sample of the compound when recrystallized from hot dimethylformamide by addition of water and dried at 80° C. had the m.p. 178°–180° C.; $[\alpha]_D^{25} = +67.4°$ (1% in pyridine).

4α,5α-Epoxy-17β-hydroxy-4,17-dimethyl-3-oxoandrostane-2α-carbonitrile when administered orally as a suspension in 1% aqueous gum tragacanth to rats at day ten of pregnancy was completely effective as an interceptive agent at a single dose of 48 mg/kg; MED$_{100}$ = 48 mg/kg. It was six times as active as its lower homolog, 4α,5α-epoxy-17β-hydroxy-17-methyl-3-oxoandrostane-2α-carbonitrile which had MED$_{100}$ = 300 mg/kg.

4α,5α-Epoxy-17β-hydroxy-4,17-dimethyl-3-oxoandrostane-2α-carbonitrile was also found to be active as an interceptive agent in rhesus monkeys. When administered orally to a group of eight monkeys beginning on approximately day 50 of pregnancy (end of first trimester) at a daily dose of 50 mg. per monkey for five days, all eight monkeys aborted. The compound also terminated pregnancy in all of a group of seven monkeys at a dose of 100 mg. per monkey per day administered for five days beginning on approximately day 26 of pregnancy.

EXAMPLE 2

4α,5α-Epoxy-3,17β-dihydroxy-4,17-dimethylandrost-2-ene-2-carbonitrile 3-acetate and
4α,5α-epoxy-3,17β-dihydroxy-4,17-dimethylandrost-2-ene-2-carbonitrile 3,17-diacetate A mixture of 6.02 g. (0.0168 m.) of 4α,5α-epoxy-17β-hydroxy-4,17-dimethyl-3-oxoandrostane-2α-carbonitrile (Example 1, part f), 20 ml. of acetic anhydride and 25 ml. of pyridine was kept at room temperature for two days. The reaction mixture was concentrated in vacuo to remove volatiles and the residue chromatographed on a 300 g. column of silica gel made up in pentane. The material was placed on the column with benzene and eluted successively with the following solvent series: 100% pentane, 2.5% ether in pentane, 10% ether in pentane, 10% ether and 10% methylene dichloride in pentane, 15% ether and 10% methylene dichloride in pentane, 20% ether and 10% methylene dichloride in pentane, 25% ether and 10% methylene dichloride in pentane, 100% ether, and 100% acetone.

The material brought out by 100% ether was recrystallized from acetonitrile to give 3.98 g. of 4α,5α-epoxy-3,17β-dihydroxy-4,17-dimethylandrost-2-ene-2-carbonitrile 3-acetate as fine colorless needles, m.p. 207°–209° C.; $[\alpha]_D^{25} = +57.7°$ (1% in chloroform).

The remaining material eluted from the chromatogram was reacetylated with acetic anhydride in pyridine, heating the mixture on a steam bath. The product isolated therefrom was crystallized from and/or slurried with ether, methylene dichloride-acetonitrile, isopropyl alcohol and dimethylformamide, and finally recrystallized from dioxane to give 2.04 g. of 4α,5α-epoxy-3,17β-dihydroxy-4,17-dimethylandrost-2-ene-2-carbonitrile, 3,17-diacetate as colorless needles, m.p. 261°–264° C.; $[\alpha]_D^{25} = +58.6°$ (1% in chloroform).

It is further contemplated that under mild alkaline conditions, e.g. with alkali metal carbonate at ambient temperatures, the 3,17-diacetate can be selectively hydrolyzed to give 4α,5α-epoxy-17β-hydroxy-4,17-dimethyl-3-oxoandrostane-2α-carbonitrile 17-acetate.

EXAMPLE 3

(a) 2-Hydroxymethylene-17β-hydroxy-4-methylandrost-4-en-3-one was prepared from 32.28 g. of 17β-hydroxy-4-methylandrost-4-en-3-one and 32 ml. of methyl formate by a procedure analogous to that of Example 1, part (c) except that sodium hydride (15 g., 50%) was used in place of sodium methoxide. The 20 g. of product obtained was used directly in the next reaction.

(b) 4-Methylandrosta-2,4-dieno[2,3-d]isoxazol-17β-ol [II; R is CH$_3$, R′ is OH, R″ and R‴ are H] was prepared from 20 g. of 2-hydroxymethylene-17β-hydroxy-4-methylandrost-4-en-3-one, 4.3 g. of hydroxylamine hydrochloride and 5 g. of sodium acetate in ethanol according to the procedure of Example 1, part (d), and obtained in 73% yield, m.p. 176°–179° C., when recrystallized from ethyl acetate.

(c) 4α,5α-Epoxy-4-methylandrost-2-eno[2,3-d]isoxazol-17β-ol [III; R is CH$_3$, R′ is OH, R″ and R‴ are H] was prepared from 32.75 g. of 4-methylandrosta-2,4-dieno[2,3-d]isoxazol-17β-ol and 21 g. of 85% m-chloroperbenzoic acid in 500 ml. of methylene dichloride according to the procedure of Example 1, part (e), and there was obtained 13.91 g. of product, m.p. 220°–226° C., recrystallized from an ethyl acetate—ethanol mixture; $[\alpha]_D^{25} = +92.5°$ (1% in chloroform).

4α,5α-Epoxy-4-methylandrost-2-eno[2,3-d]isoxazol-17β-ol was found to have MED$_{100}$ = 500 mg/kg when tested in rats for interceptive activity by oral administration at day 10 of pregnancy.

(d) 4α,5α-Epoxy-17β-hydroxy-4-methyl-3-oxoandrostane-2α-carbonitrile [I; R is CH$_3$, R′ is OH, R″ and R‴ are H] was prepared from 11.0 g. of 4α,5α-epoxy-4- methylandrost-2-eno[2,3-d]isoxazol-17β-ol and 2.26 g. of sodium methoxide according to the procedure of Example 1, part (f), and there was obtained 10.62 g. of product, m.p. 192°–193° C. when recrystallized first from an ethyl acetate—acetone mixture and then from an ethanol—ethyl acetate mixture; $[\alpha]_D^{25} = -13.4°$ (1% in chloroform).

4α,5α-Epoxy-17β-hydroxy-4-methyl-3-oxoandrostane-2α-carbonitrile when administered orally to rats at day ten of pregnancy was completely effective as an interceptive agent at a single dose of 125 mg/kg ($MED_{100}$). It was five times as active as its lower homolog, 4α,5α-epoxy-17β-hydroxy-3-oxoandrostane-2α-carbonitrile which had $MED_{100}$ = 500 mg/kg.

EXAMPLE 4

(a) 4-Methylandrosta-2,4-dieno[2,3-d]isoxazol-17-one [II; R is $CH_3$, R' and R" together are O, R''' is H]

To a stirred suspension of 52.0 g. of pyridinium chlorochromate in 1000 ml. of methylene dichloride was added a solution of 61.2 g. of 4-methylandrosta-2,4-dieno[2,3-d]isoxazol-17β-ol (Example 3b) in 1000 ml. of methylene dichloride. The reaction mixture was stirred for three hours at room temperature, an additional 25.0 g. of pyridinium chlorochromate then added, and the mixture stirred for about 16 hours longer. The resulting suspension was filtered through an alumina pad, and the filtrate was washed with 2N hydrochloric acid, water and dilute aqueous sodium bicarbonate. The organic layer was dried over anhydrous magnesium sulfate, filtered and the filtrate concentrated until crystalline material separated. The product was obtained in four crops totaling 51.2 g. The fractions with the least amount of polar impurities, as determined by thin layer chromatography, were recrystallized from acetic acid to give 11.9 g. of 4-methylandrosta-2,4-dieno[2,3-d]isoxazol-17-one, pale yellow powder, m.p. 236°–238° C.

(b) 4α,5α-Epoxy-4-methylandrost-2-eno[2,3-d]isoxazol-17-one [III; R is $CH_3$, R' and R" together are O, R''' is H] was prepared from 17.35 g. of 4-methylandrosta-2,4-dieno[2,3-d]isoxazol-17-one and 12.5 g. of m-chloroperbenzoic acid in 500 ml. of methylene dichloride according to the procedure of Example 1, part (e), and there was obtained 7 g. of product, m.p. 249°–251° C.; $[\alpha]_D^{25} = +135°$ (1% in chloroform).

4α,5α-Epoxy-4-methylandrost-2-eno[2,3-d]isoxazol-17-one when administered orally to rats at day ten of pregnancy was partially effective as an interceptive agent at a single dose of 500 mg/kg.

(c) 4α,5α-Epoxy-4-methyl-3,17-dioxoandrostane-2α-carbonitrile [I; R is $CH_3$, R' and R" together are O, R''' is H] was prepared from 15.3 g. of 4α,5α-epoxy-4-methylandrost-2-eno[2,3-d]isoxazol-17-one and 4.4 g. of sodium methoxide according to the procedure of Example 1, part (f), and there was obtained 8.5 g. of product, m.p. 235°–237° C. when recrystallized from acetonitrile; $[\alpha]_D^{25} = +41.0°$ (1% in chloroform).

4α,5α-Epoxy-4-methyl-3,17-dioxoandrostane-2α-carbonitrile when administered orally to rats at day ten of pregnancy was partially effective as an interceptive agent at a single dose of 500 mg/kg.

EXAMPLE 5

4-Methyl-3,17-dioxoandrost-4-ene-2α-carbonitrile was prepared from 25.5 g. of 4-methylandrosta-2,4-dieno[2,3-d]isoxazol-17-one (Example 4, part a) and 7.55 g. of sodium methoxide according to the procedure of Example 1, part (f), and there was obtained 11.5 g. of product, m.p. 202°–205° C. when recrystallized from acetonitrile; $[\alpha]_D^{25} = +210°$ (1% in chloroform).

By treating 4-methyl-3,17-dioxoandrost-4-ene-2α-carbonitrile with m-chloroperbenzoic acid in accordance with the procedure of Example 1, part (e), it is contemplated that 4α,5α-epoxy-4-methyl-3,17-dioxoandrostane-2α-carbonitrile, the compound of Example 4(c), will be obtained.

EXAMPLE 6

(a) 4-Methyl-17,17-(1,2-ethylenedioxy)androsta-2,4-dieno[2,3-d]isoxazole [II; R is $CH_3$, R' and R" together are —$OCH_2CH_2O$—, R''' is H]

A mixture of 39.2 g. of 4-methylandrosta-2,4-dieno[2,3-d]isoxazol-17-one (Example 4, part a), 150 ml. of ethylene glycol and 1.5 g. of p-toluenesulfonic acid in 800 ml. of benzene was heated at reflux under a water separator for about 24 hours. The reaction mixture was concentrated to remove the solvent, and the residue was taken up in a mixture of ether and methylene dichloride and washed with dilute sodium hydroxide solution. The organic layer was dried over anhydrous magnesium sulfate, filtered and concentrated to dryness. The residue was crystallized from ethanol containing a few drops of pyridine to give 30.16 g. of 4-methyl-17,17-(1,2-ethylenedioxy)androsta-2,4-dieno[2,3-d]isoxazole, m.p. 173°–175° C.

(b) 4α,5α-Epoxy-4-methyl-17,17-(1,2-ethylenedioxy)androst-2-eno-[2,3-d]isoxazole [III; R is $CH_3$, R' and R" together are —$OCH_2CH_2O$—, R''' is H] was prepared from 28.82 g. of 4-methyl-17,17-(1,2-ethylenedioxy)androsta-2,4-dieno[2,3-d]isoxazole and 16.3 g. of m-chloroperbenzoic acid in 500 ml. of methylene dichloride containing 1 ml. of pyridine, according to the procedure of Example 1, part (e), and there was obtained 25.90 g. of product, m.p. 205°–211° C.

(c) 4α,5α-Epoxy-4-methyl-17,17-(1,2-ethylenedioxy)-3-oxo-2α-carbonitrile [I; R is $CH_3$, R' and R" together are —$OCH_2CH_2O$—, R''' is H] was prepared from 25.9 g. of 4α,5α-epoxy-4-methyl-17,17-(1,2-ethylenedioxy)androst-2-eno[2,3-d]isoxazole and 7.1 g. of sodium methoxide according to the procedure of Example 1, part (f), and there was obtained 24.47 g. of product, m.p. 205°–207° C. when recrystallized from acetonitrile; $[\alpha]_D^{25} = -46.4°$ (1% in chloroform).

4α,5α-Epoxy-4-methyl-17,17-(1,2-ethylenedioxy)-3-oxo 2α-carbonitrile when administered orally to rats at day ten of pregnancy was completely effective as an interceptive agent at a single dose of 250 mg/kg ($MED_{100}$).

EXAMPLE 7

(a) 2-Hydroxymethylene-17-hydroxy-4-methyl-17α-pregn-4-en-20-yn-3-one was prepared from 65.9 g. of 17-hydroxy-4-methyl-17α-pregn-4-en-20-yn-3-one [m.p. 198°–202° C.; $[\alpha]_D^{25} = +60.2°$ (1% in chloroform)] and 64 ml. of methyl formate by a procedure analogous to that of Example 1, part (c) except that sodium hydride (19.6 g.) was used in place of sodium methoxide. A crude yield of over 90% was obtained.

(b) 4-Methyl-17α-pregna-2,4-dien-20-yno[2,3-d]isoxazol-17-ol [II; R is CH$_3$, R' is OH, R" is C≡CH, R''' is H] was prepared from 3.5 g. of 2-hydroxymethylene-17-hydroxy-4-methyl-17α-pregn-4-en-20-yn-3-one, 0.75 g. of hydroxylamine hydrochloride, 1.3 g. of sodium acetate and 50 ml. of 80% acetic acid, heated one hour at 100° C. There was obtained 1.5 g. of product, pale yellow crystals, m.p. 238°–243° C. when recrystallized from an ethanol—methylene dichloride mixture; [α]$_D^{25}$ = +0.19° (1% in chloroform).

(c) 4α,5α-Epoxy-4-methyl-17α-pregn-2-en-20-yno[2,3-d]isoxazol-17-ol [III; R is CH$_3$, R' is OH, R" is C≡CH, R''' is H] was prepared from 41.7 g. of 4-methyl-17α-pregna-2,4-dien-20-yno[2,3-d]isoxazol-17-ol and 21.6 g. of m-chloroperbenzoic acid in 1000 ml. of methylene dichloride according to the procedure of Example 1, part (e), and there was obtained about 35 g. of product, crystallized from a methylene dichloride—ethyl acetate mixture. A sample crystallized from an ethyl acetate—methanol mixture had m.p. 245°–247° C.

(d) 4α,5α-Epoxy-17-hydroxy-4-methyl-3-oxo-17α-pregn-20-yne-2α-carbonitrile [I; R is CH$_3$, R' is OH, R" is C≡CH, R''' is H] was prepared from 25 g. of 4α,5α-epoxy-4-methyl-17α-pregn-2-en-20-yno[2,3-d]isoxazol-17-ol and 8.1 g. of sodium methoxide according to the procedure of Example 1, part (f), and there was obtained 11.93 g. of product, pale yellow powder, m.p. 199°–203° C. when recrystallized from an acetone—ethyl acetate mixture; [α]$_D^{25}$ = −83.0° (1% in chloroform).

4α,5α-Epoxy-17-hydroxy-4-methyl-3-oxo-17α-pregn-20-yne-2α-carbonitrile when administered orally to rats at day ten of pregnancy was completely effective as an interceptive agent at a single dose of 200 mg/kg (MED$_{100}$).

EXAMPLE 8

4α,5α-Epoxy-17-hydroxy-4-methyl-3-oxo-17α-pregn-20-ene-2α-carbonitrile [I; R is CH$_3$, R' is OH, R" is CH=CH$_2$, R''' is H]

To a solution of 14.8 g. of 4α,5α-epoxy-17-hydroxy-4-methyl-3-oxo-17α-pregn-20-yne-2α-carbonitrile (Example 7d) in 200 ml. of ethyl acetate was added 1 g. of 10% palladium-on-carbon catalyst and the mixture was hydrogenated until the amount of hydrogen calculated to partially reduce the ethynyl group to a vinyl group was absorbed. The reaction mixture was filtered, the filtrate concentrated to dryness and the residue crystallized from an acetone-tetrahydrofuran mixture. The 12 g. of product was recrystallized from dimethylformamide by addition of water to give 10.8 g. of 4α,5α-epoxy-17-hydroxy-4-methyl-3-oxo-17α-pregn-20-ene-2α-carbonitrile, m.p. 206°–208° C.; [α]$_D^{25}$ = +82.1° (1% in pyridine).

Alternatively, 4α,5α-epoxy-17-hydroxy-4-methyl-3-oxo-17α-pregn-20-ene-2α-carbonitrile can be prepared from 17α-vinylandrost-4-en-17-ol-3-one (17-vinyltestosterone) following the synthetic sequence of Example 1.

4α,5α-Epoxy-17-hydroxy-4-methyl-3-oxo-17α-pregn-20-ene-2α-carbonitrile when administered orally to rats at day ten of pregnancy was completely effective as an interceptive agent at a single dose of 250 mg/kg (MED$_{100}$).

EXAMPLE 9

4α,5α-Epoxy-17-hydroxy-4-methyl-3-oxo-17α-pregnane-2α-carbonitrile [I; R is CH$_3$, R' is OH, R" is CH$_2$CH$_3$, R''' is H]

To a solution of 5.5 g. of 4α,5α-epoxy-17-hydroxy-4-methyl-3-oxo-17α-pregn-20-yne-2α-carbonitrile (Example 7d) in 250 ml. of tetrahydrofuran was added 0.5 g. of 10% palladium-on-carbon catalyst and the mixture was hydrogenated until the amount of hydrogen calculated to completely reduce the ethynyl group to an ethyl group (about 16 hours) was absorbed. The reaction mixture was filtered, the filtrate concentrated to dryness and the residue crystallized from aqueous dimethylformamide to give 4.15 g. of 4α,5α-epoxy-17-hydroxy-4-methyl-3-oxo-17α-pregnane-2α-carbonitrile, m.p. 210°–213° C. A sample when recrystallized from aqueous tetrahydrofuran had the m.p. 216°–217.5° C.; [α]$_D^{25}$ = +77.8° (1% in pyridine).

Alternatively, the 4α,5α-epoxy-17-hydroxy-4-methyl-3-oxo-17α-pregnane-2α-carbonitrile can be prepared from 17α-ethylandrost-4-en-17-ol-3-one (17-ethyltestosterone) following the synthetic sequence of Example 1.

4α,5α-Epoxy-17-hydroxy-4-methyl-3-oxo-17α-pregnane-2α-carbonitrile when administered orally to rats at day ten of pregnancy was completely effective as an interceptive agent at a single dose of 500 mg/kg (MED$_{100}$).

EXAMPLE 10

By replacing the 17-hydroxy-4-methyl-17α-pregn-4-en-20-yn-3-one (4-methyl-17-ethynyltestosterone) starting material in Example 7, part (a) by a molar equivalent amount of 4-methyl-17-(1-propynyl)testosterone and carrying out the subsequent transformations of Examples 7, parts (a)-(d), 8 and 9, it is contemplated that there can be prepared:

4α,5α-Epoxy-17β-hydroxy-4-methyl-17-(1-propynyl)-3-oxoandrostane-2α-carbonitrile [I; R is CH$_3$, R' is OH, R" is C≡CCH$_3$, R''' is H];

4α,5α-Epoxy-17β-hydroxy-4-methyl-17-(1-propenyl)-3-oxoandrostane-2α-carbonitrile [I; R is CH$_3$, R' is OH, R" is CH=CHCH$_3$, R''' is H]; and 4α,5α-Epoxy-17β-hydroxy-17-propyl-4-methyl-3-oxoandrostane-2α-carbonitrile [I; R is CH$_3$, R' is OH, R" is CH$_2$CH$_2$CH$_3$, R''' is H].

EXAMPLE 11

By replacing the 17-hydroxy-4-methyl-17α-pregn-4-en-20-yn-3-one (4-methyl-17-ethynyltestosterone) starting material in Example 7, part (a) by a molar equivalent amount of 4-methyl-17-(2-propynyl)testosterone and carrying out the subsequent transformations of Examples 7, parts (a)-(d), and 8, it is contemplated that there can be prepared:

4α,5α-Epoxy-17β-hydroxy-4-methyl-17-(2-propynyl)-3-oxoandrostane-2α-carbonitrile [I; R is CH$_3$, R' is OH, R" is CH$_2$C≡CH, R''' is H]; and 4α,5α-Epoxy-17β-hydroxy-17-allyl-4-methyl-3-oxoandrostane-2α-carbonitrile [I; R is CH$_3$, R' is OH, R" is CH$_2$CH=CH$_2$, R''' is H].

The latter compound can also be prepared from 17α-allylandrost-4-en-17-ol-3-one (17-allyltestosterone) following the synthetic sequence of Example 1.

EXAMPLE 12

(a) 17β-Hydroxy-2-hydroxymethylene-6α-methylandrost-4-en-3-one was prepared from 286 g. of 17β-hydroxy-6α-methylandrost-4-en-3-one (6α-methyltestosterone), 410 ml. of methyl formate, 140 g. of sodium methoxide, 40 ml. of methanol and 3 l. of tetrahydrofuran according to the procedure of Example 1, part (c). The total product, obtained nearly quantitative yield as an amber glass was used directly in the next reaction.

(b) 6α-methylandrosta-2,4-dieno[2,3-d]isoxazol-17β-ol [II; R and R' are H, R" is OH, R'" is α-$CH_3$] was prepared from 312 g. of 17β-hydroxy-2-hydroxymethylene-6α-methylandrost-4-en-3-one, 75 g. of hydroxylamine hydrochloride, 135 g. of sodium acetate trihydrate and 3 l. of glacial acetic acid according to the procedure of Example 1, part (d), and there was obtained 181 g. of product, m.p. 180°–183° C. when crystallized from isopropyl alcohol. A sample when recrystallized from isopropyl acetate had the m.p. 188°–190° C.

(c) 4α,5α-Epoxy-6α-methylandrost-2-eno[2,3-d]isoxazol-17β-ol [III; R and R' are H, R" is OH, R'" is α-$CH_3$] was prepared from 181 g. of 6α-methylandrosta-2,4-dieno[2,3-d]isoxazol-17β-ol and 128 g. of m-chloroperbenzoic acid in 2.5 l. of methylene dichloride according to the procedure of Example 1, part (e), and there was obtained 127 g. of product, m.p. 212°–214° C. when slurried with isopropyl acetate. A sample when recrystallized from ethyl acetate had the m.p. 220°–222° C.

4α,5α-Epoxy-6α-methylandrost-2-eno[2,3-d]isoxazol-17β-ol when administered orally to rats at day ten of pregnancy showed activity as an interceptive agent at a single dose of 500 mg/kg.

(d) 4α,5α-Epoxy-17β-hydroxy-6α-methyl-3-oxoandrostane-2α-carbonitrile [I; R and R' are H, R" is OH, R'" is α-$CH_3$]

A solution of 44 g. of 85% potassium hydroxide in 950 ml. of water was cooled to room temperature and a suspension of 127 g. of 4α,5α-epoxy-6α-methylandrost-2-eno[2,3-d]isoxazol-17β-ol in 1 l. of tetrahydrofuran was added and rinsed in with 300 ml. of tetrahydrofuran. The reaction mixture was stirred for about 16 hours and allowed to stand for three days at room temperature. The reaction mixture was filtered and slowly poured into an ice bath-cooled mixture of 250 ml. of concentrated hydrochloric acid and 3 l. of water. The product which separated and crystallized upon stirring was collected, washed with water and dissolved in hot dimethylformamide. The latter solution was filtered, diluted nearly to cloudiness with warm water and cooled in an ice bath. The solid product which separated was collected and dried in vacuo at 55° C. to give 88 g. of 4α,5α-epoxy-17β-hydroxy-6α-methyl-3-oxoandrostane-2α-carbonitrile, m.p. 246°–249° C.

4α,5α-Epoxy-17β-hydroxy-6α-methyl-3-oxoandrostane-2α-carbonitrile when administered orally to rats at day ten of pregnancy was completely effective as an interceptive agent at a single dose of 10 mg/kg ($MED_{100}$), and is fifty times as active as the lower homolog, 4α,5α-epoxy-17β-hydroxy-3-oxoandrostane-2α-carbonitrile ($MED_{100}$ = 500 mg/kg).

By replacing the 17β-hydroxy-6α-methylandrost-4-en-3-one starting material in Example 12, part (a) by a molar equivalent amount of 17β-hydroxy-6α,17-dimethylandrost-4-en-3-one and carrying out the transformations of Example 12, parts (a)-(d), it is contemplated that 4α,5α-epoxy-17β-hydroxy-6α,17-dimethyl-3-oxoandrostane-2α-carbonitrile [I; R is H, R' is $CH_3$, R" is OH, R'" is α-$CH_3$] can be prepared.

EXAMPLE 13

(a) 17β-Hydroxy-2-hydroxymethylene-4,6β-dimethylandrost-4-en-3-one was prepared from 28.1 g. of 17β-hydroxy-4,6β-dimethylandrost-4-en-3-one [Burn et al., *Tetrahedron* 19, 1762 (1963)], 24.9 g. of methyl formate and 11.4 g. of sodium methoxide according to the procedure of Example 1, part (c), and there was obtained 24.8 g. of solid product used directly in the next reaction.

(b) 4,6β-Dimethylandrosta-2,4-dieno[2,3-d]isoxazol-17β-ol [II; R is $CH_3$, R' is OH, R" is H, R'" is β-$CH_3$] was prepared from 20.8 g. of 17β-hydroxy-2-hydroxymethylene-4,6β-dimethylandrost-4-en-3-one, 4.4 g. of hydroxylamine hydrochloride, 8.2 g. of sodium acetate trihydrate and 250 ml. of acetic acid according to the procedure of Example 1, part (d), and there was obtained 19.9 g. of product as a colorless solid.

(c) 4α,5α-Epoxy-4,6β-dimethylandrost-2-eno[2,3-d]isoxazol-17β-ol [III; R is $CH_3$, R' is OH, R" is H, R'" is β-$CH_3$] was prepared from 23.2 g. of 4,6β-dimethylandrosta-2,4-dieno[2,3-d]isoxazol-17β-ol and 15.8 g. of m-chloroperbenzoic acid in 320 ml. of methylene dichloride according to the procedure of Example 1, part (e). The crude product was chromatographed by Water's LC#500 high pressure liquid chromatography procedure and eluted with n-hexane containing increasing amounts of ethyl acetate to give 17.4 g. of epoxidized product, used directly in the next reaction.

(d) 4α,5α-Epoxy-17β-hydroxy-4,6β-dimethyl-3-oxoandrostane-2α-carbonitrile [I; R is $CH_3$, R' is OH, R" is H, R'" is β-$CH_3$] was prepared from 17.4 g. of 4α,5α-epoxy-4,6β-dimethylandrost-2-eno[2,3-d]isoxazol-17β-ol and 7.88 g. of sodium methoxide in 400 ml. of tetrahydrofuran according to the procedure of Example 1, part (f), and there was obtained 15.4 g. of product, m.p. 231°–232° C. when recrystallized from aqueous dimethylformamide; $[\alpha]_D^{25} = -70.5°$ (1% in chloroform).

4α,5α-Epoxy-17β-hydroxy-4,6β-dimethyl-3-oxoandrostane-2α-carbonitrile when administered orally to rats at day ten of pregnancy was completely effective as an interceptive agent at a single dose of 500 mg/kg ($MED_{100}$).

By replacing the 17β-hydroxy-4,6β-dimethylandrost-4-en-3-one starting material in Example 13, part (a) by a molar equivalent amount of 17β-hydroxy-4,6β,17-trimethylandrost-4-en-3-one (Burn et al., loc. cit.) and carrying out the transformations of Example 13, parts (a)-(d), it is contemplated that 4α,5α-epoxy-17β-hydroxy-4,6β,17-trimethyl-3-oxoandrostane-2α-carbonitrile [I; R and R" are $CH_3$, R' is OH, R'" is β-$CH_3$] can be prepared.

I claim:

1. A compound of the formula

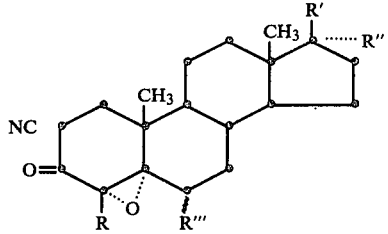

wherein
R is hydrogen or methyl;
R' is hydroxy or lower-alkanoyloxy;
R" is lower-alkyl, lower-alkenyl or loweralkynyl; or R' and R" together represent ethylenedioxy;
R'" is hydrogen or methyl; or 3-enol lower-alkanoate esters thereof; with the proviso that when R is hydrogen, R'" is α-methyl; and when R is methyl, R'" is hydrogen or β-methyl.

2. A compound according to claim 1 wherein R is methyl, R' is hydroxy and R'" is hydrogen.

3. 4α,5α-Epoxy-17β-hydroxy-4,17-dimethyl-3-oxoandrostane-2α-carbonitrile, according to claim 2.

4. 4α,5α-Epoxy-3,17β-dihydroxy-4,17-dimethylandrost-2-ene-2-carbonitrile 3-acetate, according to claim 2.

5. 4α,5α-Epoxy-3,17β-dihydroxy-4,17-dimethylandrost-2-ene-2-carbonitrile, 3,17-diacetate, according to claim 1.

6. 4α,5α-Epoxy-17-hydroxy-4-methyl-3-oxo-17α-pregn-20-yne-2α-carbonitrile, according to claim 2.

7. 4α,5α-Epoxy-17-hydroxy-4-methyl-3-oxo-17α-pregn-20-ene-2α-carbonitrile, according to claim 2.

8. 4α,5α-Epoxy-17-hydroxy-4-methyl-3-oxo-17α-pregnane-2α-carbonitrile, according to claim 2.

9. 4α,5α-Epoxy-4-methyl-17,17-(1,2-ethylenedioxy)-3-oxo-2α-carbonitrile, according to claim 1.

10. 4α,5α-Epoxy-17β-hydroxy-4,6β-dimethyl-3-oxoandrostane-2α-carbonitrile.

11. A process for preparing a compound according to claim 1 from a compound of the formula

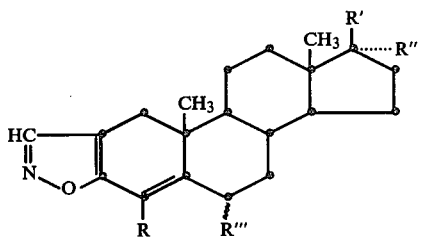

wherein R, R', R" and R'" have the meanings given in claim 1, by epoxidizing the 4,5-double bond with hydrogen peroxide or a peracid, and cleaving the isoxazole ring with a base to produce the cyanoketone, the reactions being carried out in either order.

12. A composition for disrupting pregnancy in a female mammal which comprises an interceptively effective amount of a compound according to claim 1 incorporated in a pharmaceutical carrier suitable for oral administration.

13. A composition according to claim 12 wherein the compound is 4α,5α-epoxy-17β-hydroxy-4,17-dimethyl-3-oxoandrostane-2α-carbonitrile.

14. A method for disrupting pregnancy in a female mammal which comprises administering orally to said mammal, subsequent to implantation of a fertilized ovum in said mammal, an interceptively effective amount of a compound according to claim 1.

15. A method according to claim 14 wherein the compound is 4α,5α-epoxy-17β-hydroxy-4,17-dimethyl-3-oxoandrostane-2α-carbonitrile.

16. A compound of the formula

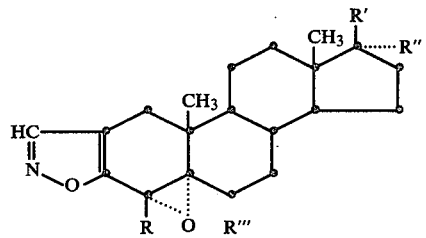

wherein:
R is hydrogen or methyl;
R' is hydroxy;
R" is hydrogen, lower-alkyl, lower-alkenyl or lower-alkynyl; or R' and R" together represent oxo or ethylenedioxy; and
R'" is hydrogen or methyl; with the proviso that when R is hydrogen, R'" is α-methyl; and when R is methyl, R'" is hydrogen or β-methyl.

17. 4α,5α-Epoxy-4,17-dimethylandrost-2-eno[2,3-d]isoxazol-17β-ol, according to claim 16.

18. 4α,5α-Epoxy-4-methylandrost-2-eno[2,3-d]isoxazol-17β-ol, according to claim 16.

19. 4α,5α-Epoxy-4-methylandrost-2-eno[2,3-d]isoxazol-17-one, according to claim 16.

20. 4α,5α-Epoxy-6α-methylandrost-2-eno[2,3-d]isoxazol-17β-ol, according to claim 16.

21. 4-Methylandrosta-2,4-dieno[2,3-d]isoxazol-17-one.

22. 4-Methyl-3,17-dioxoandrost-4-ene-2α-carbonitrile.

* * * * *

UNITED STATES PATENT AND TRADEMARK OFFICE
CERTIFICATE OF CORRECTION

PATENT NO. : 4,160,027
DATED : July 3, 1979
INVENTOR(S) : Robert G. Christiansen It is certified that error appears in the above-identified patent and that said Letters Patent are hereby corrected as shown below:

Column 3, line 40, "(OCHC=)" should read --(OHCH=)--.

Column 5, line 24, "catalysts" should read --catalyst--; line 55, "20°-50°C." should read --20-25°C.--.

Column 8, line 28, delete the comma (,) after "carbonitrile".

Column 15, Claim 1,

" 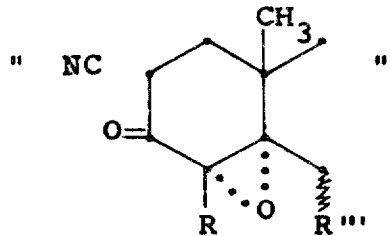 "  should read -- 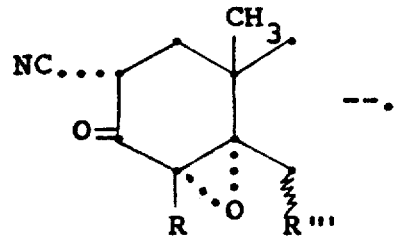 --.

Column 15, line 15, Claim 1, "loweralkynyl" should read --lower-alkynyl--.

Column 15, line 28, Claim 5, delete the comma (,) after "carbonitrile".

UNITED STATES PATENT AND TRADEMARK OFFICE
CERTIFICATE OF CORRECTION

PATENT NO. : 4,160,027

DATED : July 3, 1979

INVENTOR(S) : Robert G. Christiansen

It is certified that error appears in the above-identified patent and that said Letters Patent are hereby corrected as shown below:

Column 16, Claim 16,

" 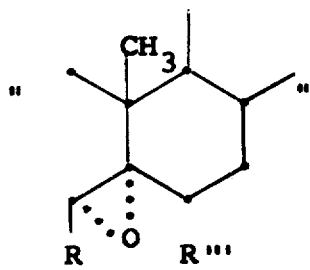 " should read -- 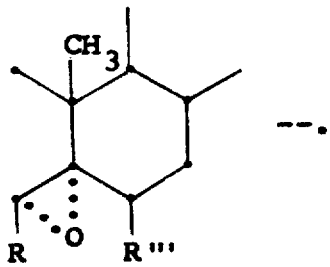 --.

Signed and Sealed this

Ninth Day of October 1979

[SEAL]

Attest:

RUTH C. MASON
Attesting Officer

LUTRELLE F. PARKER
Acting Commissioner of Patents and Trademarks